United States Patent [19]

Teraji et al.

[11] Patent Number: 4,493,832
[45] Date of Patent: Jan. 15, 1985

[54] CERTAIN GLYCEROL-PHOSPHORYL CHOLINE DERIVATIVES, COMPOSITIONS CONTAINING SAME AND METHOD OF USING SAME

[75] Inventors: Tsutomu Teraji, Osaka; Eishiro Todo, Toyonaka; Norihiko Shimazaki, Suita; Teruo Oku, Osaka; Takayuki Namiki, Minoo, all of Japan

[73] Assignee: Fujisawa Pharmaceutical Co., Ltd., Osaka, Japan

[21] Appl. No.: 391,918

[22] Filed: Jun. 24, 1982

[30] Foreign Application Priority Data

Jul. 3, 1981 [GB] United Kingdom ............... 8120612

[51] Int. Cl.$^3$ ...................... C07F 9/141; C07F 9/143; A61K 31/685
[52] U.S. Cl. .................................. 424/199; 260/941; 546/22; 424/200
[58] Field of Search ................. 546/22; 424/200, 199; 260/941

[56] References Cited

U.S. PATENT DOCUMENTS 3,542,820 11/1970 Rakhit .................. 260/403
3,577,446 5/1971 Rakhit .................. 260/403

FOREIGN PATENT DOCUMENTS 0043472 1/1982 European Pat. Off. ............ 260/399
2020663 11/1979 United Kingdom ............... 260/942

OTHER PUBLICATIONS

Orchin et al., "The Vocabulary of Organic Chemistry", pp. 469, Wiley-Interscience, 1980.
Chemical Abstracts, vol. 93, No. 3, 21st Jul. 1980, pp. 653, 25917n.
Chemical Abstracts, vol. 88, No. 7, 13th Feb. 1978, pp. 559, No. 50965f, Robinson et al., "Phosphonolipids XXVII, Synthesis of Phosphonic Acid Analogs of Saturated and Unsaturated L-alpha-lecithins", and Can. J. Biochem., 1977, 55(8), 907-910.

*Primary Examiner*—Alan L. Rotman
*Attorney, Agent, or Firm*—Oblon, Fisher, Spivak, McClelland & Maier

[57] ABSTRACT

New phospholipid derivatives represented by the formula:

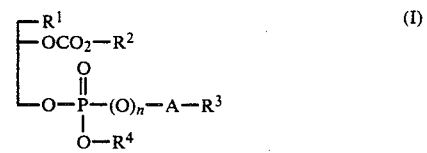

wherein $R^1$ is alkyl, alkoxy, alkylthio, ar(lower)alkoxy or alkanoylamino; $R^2$ is lower alkyl or ar(lower)alkyl; n is an integer of 0 or 1; A is lower alkylene; $R^3$ is pyridinio or a group of the formula:

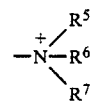

in which $R^5$, $R^6$ and $R^7$ are each hydrogen or lower alkyl; and $R^4$ is hydrogen or lower alkyl; and pharmaceutically acceptable salt thereof, which exhibit antihypertensive activity.

7 Claims, No Drawings

CERTAIN GLYCEROL-PHOSPHORYL CHOLINE DERIVATIVES, COMPOSITIONS CONTAINING SAME AND METHOD OF USING SAME

This invention relates to phospholipid derivatives. More particularly, it relates to new phospholipid derivatives which have antihypertensive activity, to processes for the preparation thereof, and to pharmaceutical composition comprising the same for therapeutical treatment of hypertention in human beings.

Accordingly, one object of this invention is to provide new and useful phospholipid derivatives.

Another object of this invention is to provide processes for the preparation of phospholipid derivatives.

A further object of this invention is to provide useful pharmaceutical composition comprising said phospholipid derivatives as antihypertensive agents.

Still further object of the present invention is to provide a therapeutical method of treating hypertention.

The object phospholipid derivatives of the present invention are novel and include the compound of the formula (I):

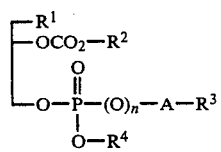

wherein
R$^1$ is alkyl, alkoxy, alkylthio, ar(lower)alkoxy or alkanoylamino;
R$^2$ is lower alkyl or ar(lower)alkyl;
n is an integer of 0 or 1;
A is lower alkylene;
R$^3$ is pyridinio or a group of the formula:

in which R$^5$, R$^6$ and R$^7$ are each hydrogen or lower alkyl; and
R$^4$ is hydrogen or lower alkyl;
and pharmaceutically acceptable salt thereof.

In the above and subsequent description of the present specification, suitable examples and illustrations for the various definitions to be included within the scope of the invention are explained in details as follows.

The term "lower" is intended to mean 1 to 6 carbon atom(s) and the term "higher" is intended to mean 7 to 25 carbon atoms, unless otherwise indicated.

Suitable "alkyl" for R$^1$ is straight or branched one containing 1 to 25 carbon atoms and may include methyl, ethyl, propyl, isopropyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl and the like, and preferably the ones containing 1 to 15 carbon atoms Suitable "alkoxy" for R$^1$ may include alkyl-O-groups wherein the alkyl moiety is the same as defined above, and preferably the ones containing 5 to 20 carbon atoms.

Suitable "alkylthio" for R$^1$ may include alkyl-S-groups wherein the alkyl moiety is the same as defined above.

Suitable "aryl" moiety in the "ar(lower)alkoxy" for R$^1$ and "ar(lower)alkyl" for R$^2$ may include phenyl, tolyl, xylyl, mesityl, cumenyl, naphthyl and the like.

Suitable "lower alkyl" for R$^2$, R$^4$, R$^5$, R$^6$ and R$^7$ and "lower alkyl" moiety in the "ar(lower)alkyl" for R$^2$ is straight or branched one containing 1 to 6 carbon atoms and may include methyl, ethyl, propyl, isopropyl, butyl, isobutyl, tert-butyl, pentyl, hexyl and the like.

Suitable "lower alkoxy" moiety in the "ar(lower)alkoxy" for R$^1$ may include lower alkyl-O-groups wherein the lower alkyl group is the same as defined above.

Suitable "alkanoyl" moiety in the "alkanoylamino" for R$^1$ is straight or branched one containing 1 to 25 carbon atoms and may include formyl, acetyl, propionyl, butyryl, isobutyryl, valeryl, isovaleryl, pivaloyl, hexanoyl, heptanoyl, octanoyl, nonanoyl, decanoyl, undecanoyl, dodecanoyl, tridecanoyl, tetradecanoyl, pentadecanoyl, hexadecanoyl heptadecanoyl, octadecanoyl, nonadecanoyl, eicosanoyl, heneicosanoyl, docosanoyl, tricasanoyl, tetracosanoyl, pentacosanoyl and the like.

Suitable "lower alkylene" for A is straight or branched one containing 2 to 6 carbon atoms and may include ethylene, trimethylene, propylene, tetramethylene, pentamethylene, hexamethylene and the like.

Suitable pharmaceutically acceptable salts of the object compounds (I) are conventional non-toxic salts and may include an inorganic acid salt (e.g. hydrochloride, hydrobromide, hydroiodide, sulfate, etc.), an organic acid salt (e.g. trifluoroacetate, sulfate, tosylate, benzenesulfonate, etc.), hydroxide ion, or a metal salt such as an alkali metal salt (e.g. sodium salt, potassium salt, etc.).

It is to be noted that the pharmaceutically acceptable salt of the object compound (I) where R$^4$ is hydrogen atom includes an zwitter ion and intramolecular salt illustrated by the formula (I') and (I'').

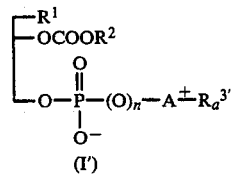 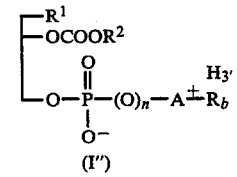

[wherein R$^1$, R$^2$, n and A are each as defined above, R$_a^{3'}$ is pyridinio or a formula

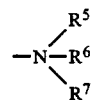

(in which R$^5$, R$^6$, and R$^7$ are each as defined above), and R$_b^{3'}$ is a formula

(in which R$^5$ and R$^6$ are each as defined above)].

With regard to the object compounds [I], it is to be noted that the compounds [I] include all of the possible optical isomers due to the asymmetric carbon atom in the molecule of the compounds [I].

And further, it is to be noted that all of the chemical formulas of the 1,2-propanediol moiety are shown by formula (A) in this specification instead of formula (B) for abbreviation.

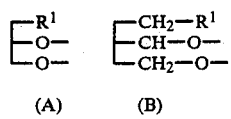

The object compound (I) and its salt of the present invention can be prepared by the following processes.

Process 1

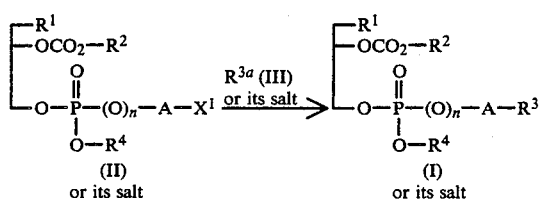

Process 2

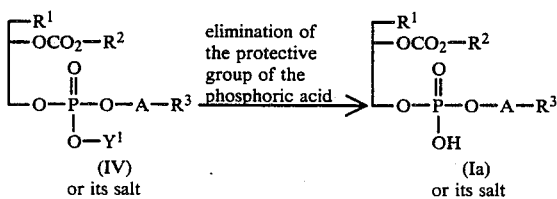

Process 3

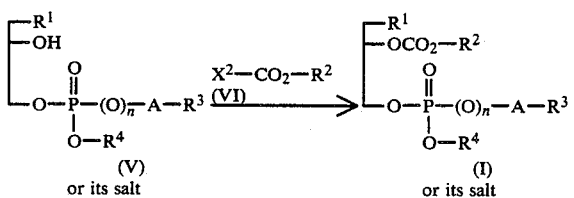

Process 4

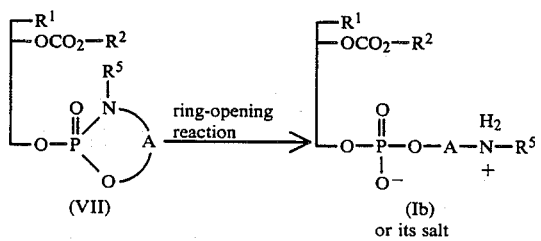

wherein $R^1$, $R^2$, n, A, $R^3$, $R^4$ and $R^5$ are each as defined above, $R^{3a}$ is pyridine or a compound of the formula:

in which $R^5$, $R^6$ and $R^7$ are each as defined above, $X^1$ and $X^2$ are each an acid residue, and $Y^1$ is a protective group of phosphoric acid.

Suitable "acid residue" for $X^1$ and $X^2$ may include halogen (e.g. fluorine, chlorine, bromine, iodine), azido, acyloxy (e.g. benzenesulfonyloxy, toxyloxy, etc.), and the like.

Suitable "protective group of phosphoric acid" for $Y^1$ may include conventional protective groups such as lower alkyl (e.g. methyl, ethyl, propyl, etc.), ar(lower)alkyl (e.g. benzyl, phenethyl, benzhydryl, trityl, etc.), phenyl, or the like.

The processes for preparing the object compounds (I) and salts thereof of the present invention are explained in detail in the following.

PROCESS 1

The object compound (I) and its salt can be prepared by reacting a compound (II) or its salt with a compound (III) or its salt.

The suitable salts of the compound (II) can be referred to the metal salts as exemplified for the compound (I).

The suitable salts of the compound (III) can be referred to the inorganic or organic acid salts as exemplified for the compound (I).

This reaction is usually carried out in a solvent such as acetone, methanol, tetrahydrofuran, chloroform, benzene or any other solvent which does not adversely affect to the reaction.

When the compound (III) or its salt is a liquid, this reaction can be carried out by using the compound (III) or its salt as a solvent.

The reaction temperature is not critical and the reaction is preferably carried out at ambient temperature or under heating.

In case that the object compound (I) is obtained in a salt form in the present reaction, the resulting salt can be converted to its free form by means of an ion exchange resin or by treatment of the salt with silver acetate, or the like.

PROCESS 2

The compound (Ia) and its salt can be prepared by subjecting a compound (IV) or its salt to the elimination reaction of the protective group $Y^1$ of the phosphoric acid.

Suitable salts of the compound (IV) can be referred to the inorganic or organic acid salts as exemplified for the compound (I).

Suitable salts of the compound (Ia) can be referred to those as exemplified for the compound (I).

The present elimination reaction is carried out in accordance with a conventional method such as hydrolysis, reduction or the like, among which preferably by treating a compound (IV) or its salt with a metal halide (e.g. sodium iodide, lithium bromide, etc.).

This reaction is usually carried out in a solvent which does not adversely affect the reaction.

The reaction temperature is not critical and the reaction is preferably carried out at ambient temperature or under heating.

In case that the object compound (Ia) is obtained in a salt form, the resulting salt can be converted to its free form according to the procedures as described in the above Process 1.

PROCESS 3

The object compound (I) and its salt can be prepared by reacting a compound (V) or its salt with a compound (VI).

Suitable salts of the compound (V) can be referred to those as exemplified for the compound (I).

This reaction is preferably carried out in the presence of a base, for example, an organic or inorganic base such as tri(lower)alkylamine (e.g. trimethylamine, triethylamine, etc.), pyridine, alkali metal bicarbonate (e.g. sodium bicarbonate), or the like.

The reaction is usually carried out in a solvent such as methylene chloride, chloroform, acetonitrile or any other solvent which does not adversely affect the reaction.

The reaction temperature is not critical and the reaction is preferably carried out under cooling, at ambient temperature or under warming.

In case that the object compound (I) is obtained in a salt form in the present reaction, the resulting salt can be converted to its free form according to the procedures as described in Process 1.

PROCESS 4

The object compound (Ib) and its salt can be prepared by subjecting a compound (VII) to the ring-opening reaction.

This reaction is carried out in accordance with a conventional method such as hydrolysis, especially by using an acid. Suitable acid may include an organic acid (e.g. formic acid, acetic acid, trifluoroacetic acid, propionic acid, etc.) and an inorganic acid (e.g. hydrochloric acid, hydrobromic acid, etc.).

The hydrolysis is usually carried out in a solvent such as methanol, water or a mixture thereof or any other solvent which does not adversely affect the reaction.

The reaction temperature is not critical and the reaction is preferably carried out under cooling, at ambient temperature or under warming.

In case that the object compound (Ib) is obtained in a salt form, the resulting salt can be converted to its free form according to the procedures as described in Process 1.

In case that the object compound (I) has an ammonio group and/or a free phosphoric acid group in its molecule, it may be transformed into its pharmaceutically acceptable salt as aforementioned by a conventional method.

The object compound prepared by the above-mentioned processes can be isolated from the reaction mixture and purified by a conventional method.

The starting compounds (II), (IV) and (VII) are novel and can be prepared by the following processes.

Process A

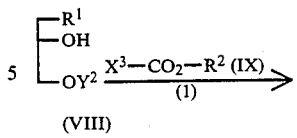

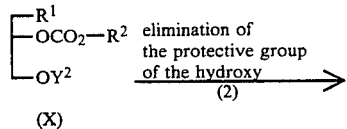

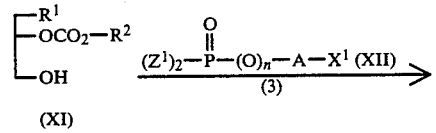

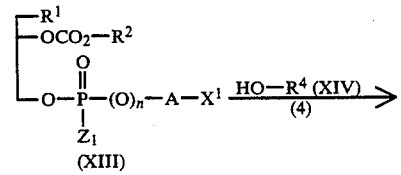

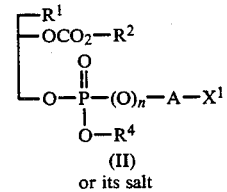

Process B

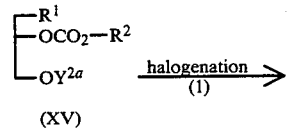

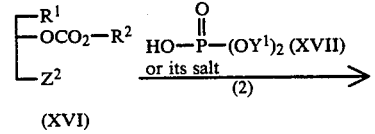

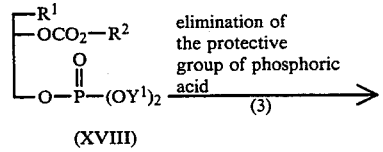

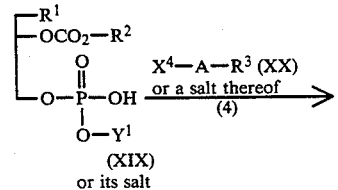

-continued

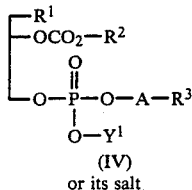

(IV) or its salt

Process C

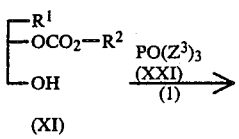

(XI)

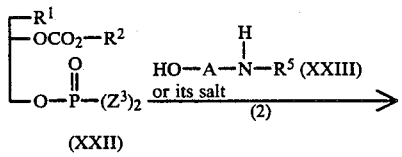

(XXII)

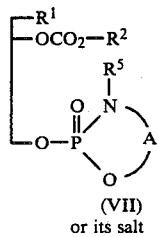

(VII) or its salt wherein
R$^1$, R$^2$, R$^3$, n, A, R$^4$, R$^5$, X$^1$ and Y$^1$ are each as defined above;
Y$^2$ is a protective group of hydroxy,
Y$^{2a}$ is hydrogen or a protective group of hydroxy,
X$^3$ and X$^4$ are each an acid residue, and
Z$^1$, Z$^2$ and Z$^3$ are each halogen.

Suitable "protective group of hydroxy" for Y$^2$ and Y$^{2a}$ may be a conventional protective group such as acyl (e.g. formyl, acetyl, tosyl, etc.), ar(lower)alkyl (e.g. benzyl, trityl, etc.) and the like.

Suitable "halogen" for Z$^1$, Z$^2$ and Z$^3$ may include chlorine, bromine, fluorine and iodine.

The processes for preparing the starting compound of the present invention are explained in detail in the following.

PROCESS A (A-1): The compound (X) can be prepared by reacting a compound (VIII) with a compound (IX).

This reaction can be carried out substantially in the same manner as the aforementioned Process 3.

(A-2): The compound (XI) can be prepared by subjecting a compound (X) to the elimination reaction of the protective group of the hydroxy.

The present elimination reaction is carried out in accordance with a conventional method such as hydrolysis, reduction, elimination using a Lewis acid or the like. Among these methods, hydrolysis is a preferable method. The hydrolysis may include a method using an acid as exemplified in Process 4.

The present elimination reaction is usually carried out in a solvent such as methylene chloride or any other solvent which does not adversely affect the reaction.

The reaction temperature is not critical and the reaction is preferably carried out under cooling, at ambient temperature or under warming.

(A-3): The compound (XIII) can be prepared by reacting a compound (XI) with a compound (XII).

This reaction can be carried out substantially in a similar manner to the aforementioned Process 3.

The compound (XIII) can be used directly in the next step reaction [i.e. process A-4)] without isolation. A-4): The compound (II) and its salt can be prepared by reacting a compound (XIII) with a compound (XIV).

This reaction may be carried out in the presence of a base as exemplified in Process 3.

The reaction is usually carried out in a solvent such as chloroform or any other solvent which does not adversely affect the reaction.

The reaction temperature is not critical and the reaction is preferably carried out under cooling, at ambient temperature or under warming.

PROCESS B (B-1): The compound (XVI) can be prepared by halogenating a compound (XV).

This reaction may be carried out by using a halogenating agent such as metal halide (e.g. sodium iodide, patassium iodide, lithium iodide, etc.) or the like.

The reaction is usually carried out in a solvent such as acetone or any other solvent which does not adversely affect the reaction.

The reaction temperature is not critical and the reaction is preferably carried out under cooling, at ambient temperature or under heating.

(B-2): The compound (XVIII) can be prepared by reacting a compound (XVI) with a compound (XVII) or its salt.

Suitable salts of the compound (XVII) include the metal salts as exemplified for the compound (I), heavy metal salts (e.g. silver salt, etc.), and the like.

This reaction may be carried out in the presence of a base as exemplified in Process 3.

The reaction is usually carried out in a solvent such as xylene or any other solvent which does not adversely affect the reaction.

The reaction temperature is not critical and the reaction is preferably carried out at ambient temperature or under heating.

(B-3): The compound (XIX) and its salt can be prepared by subjecting a compound (XVIII) to the elimination reaction of the protective group of phosphoric acid.

This reaction can be carried out substantially in the same manner as aforementioned Process 2.

In case that the compound (XIX) is obtained in a free form or an alkali metal salt form, it is preferred to convert it to a heavy metal salt (e.g. silver salt, etc.) according to a conventional method.

(B-4): The compound (IV) and its salt can be prepared by reacting a compound (XIX) or its salt with a compound (XX) or its salt.

Suitable salts of the compound (XIX) include the metal salts as exemplified for the compound (I), heavy metal salts (e.g. silver salt, etc.) and the like.

Suitable salt of the compound (XX) may be the inorganic or organic acid salts as exemplified for the compound (I) or a salt with picric acid.

This reaction is usually carried out in a solvent such as xylene, acetonitril or any other solvent which does not adversely affect the reaction.

The reaction temperature is not critical and the reaction is preferably carried out at ambient temperature or under heating.

The compound (IV) and its salt can be used directly in the next step reaction [i.e. Process 2] without isolation.

PROCESS C (C-1): The compound (XXII) can be prepared by reacting a compound (XI) with a compound (XXI).

This reaction may be carried out in the presence of a base as exemplified in Process 3.

The reaction is usually carried out in a solvent such as chloroform or any other solvent which does not adversely affect the reaction.

The reaction temperature is not critical and the reaction is preferably carried out under cooling, at ambient temperature or under warming.

The compound (XXII) can be used directly in the next step reaction [i.e. process C-2)] without isolation.

(C-2): The compound (VII) and its salt can be prepared by reacting a compound (XXII) with a compound (XXIII) or its salt.

Suitable salts of the compound (XXIII) may be an inorganic or organic acid salt as exemplified for the compound (I).

This reaction can be carried out substantially in the same manner as the above Process (C-1).

The compound (VII) can be used directly in the next step reaction [i.e. process 4] without isolation.

Among the starting compound (V), (rac)-1-O-octadecyl-glycerol-3-phosphorylcholine [the starting compound in Example 8] is described in German O.S. 2009342 and the other compounds (V) can be prepared by similar methods thereto.

The following pharmacological test data show that the object compounds (I) of the present invention exhibit high antihypertensive activity and accordingly are useful as a anti hypertensive-agent.

TEST METHOD

Male Wistar rats, aged 4 weeks, were anesthetized with i.p. pentobarbital sodium 50 mg/kg, and a silver clip, lumen width 0.22 mm, was applied to the left renal artery. Animals with mean blood pressure of 160–240 mmHg were used for experiment between 6 and 11 weeks after surgery. Blood pressure was measured directly from the left femoral artery. Ten mg/kg of each drug was administered orally.

TEST COMPOUNDS (1) (rac)-1-O-octadecyl-2-O-methoxycarbonyl-glycerol-3-phosphorylcholine.
(2) (rac)-1-O-Dodecyl-2-O-methoxycarbonyl-glycerol-3-phosphorylcholine.
(3) (rac)-1-O-tetradecyl-2-O-methoxycarbonyl-glycerol-3-phosphorylcholine.
(4) (rac)-1-O-Decyl-2-O-methoxycarbonyl-glycerol-3-phosphorylcholine.

TEST RESULTS

Mean ratios of Δmaximum decrease of blood pressure (%) are shown in the following table.

| Test compound | Mean ratio of Δmaximum decrease (%) |
| --- | --- |
| (1) | 43.1 |
| (2) | 41.8 |
| (3) | 45.3 |
| (4) | 46.9 |

As being apparent from the above test results, the object compound (I) of the present invention is useful for the antihypertensive medicine.

The effective ingredient may usually be administered with a dose of 0.1 mg/kg to 500 mg/kg, 1 to 4 times a day in a preparations such as tablet, granule, powder, capsule, syrup, injection, suppository and the like. However, the above dosage may be increased or decreased according to the age, weight or conditions of the patient or the administering method. The above mentioned pharmaceutical preparations can be prepared in a conventional manner by using conventional carriers and additives.

The present invention is illustrated by the following Examples in more detail.

Preparation 1

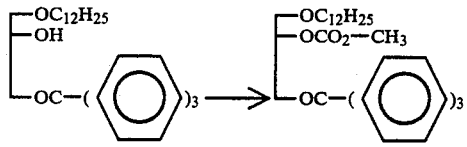

To a solution of (rac)-1-O-dodecyl-3-O-trityl-glycerol (16.0 g) and dry pyridine (7.54 g) in dry methylenechloride (200 ml) was added, dropwise over 20 minutes, a solution of methyl chloroformate (5.70 g) in dry methylene chloride (40 ml) at 5° C. After 3 hours, the solution was allowed to stand for 17 hours at ambient temperature, and then washed with aqueous hydrochloric acid and water, dried, and evaporated. The residue was purified by column chromatography on silica gel (240 g, elution by chloroform) to yield 17.33 g of (rac)-1-O-dodecyl-2-O-methoxycarbonyl-3-O-trityl-glycerol as a colorless oil.

IR (film): 2950, 2850, 1745, 1590 cm$^{-1}$.

PREPARATION 2

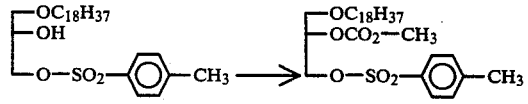

To a solution of (rac)-1-O-octadecyl-glycerol-3-tosylate (4.49 g) and dry pyridine (1.19 g) in dry methylene chloride (50 ml) was added a solution of methyl chloroformate (1.19 g) in dry methylene chloride (10 ml) over 20 minutes at 0° to 5° C.

After the addition was completed, the resulting solution was allowed to warm to ambient temperature and stirred for 13 hours. The mixture was then washed with aqueous hydrochloric acid and water, dried, and evaporated under reduced pressure. The oily residue was crystallized from methanol to yield 3.62 g of (rac)-1-O-octadecyl-2-O-methoxycarbonyl-glycerol-3-tosylate as a white solid.

m.p. 51° to 54° C.

I.R. (nujol): 1750, 1450, 1265, 1180 cm$^{-1}$.

N.M.R. (CDCl$_3$)ppm 0.8~1.66 (35H, m), 2.48 (3H, s), 3.30~3.80 (4H, m), 3.76 (3H, s), 4.25 (2H, d, J=5 Hz), 4.93 (1H, m), 7.36 (2H, d, J=8 Hz), 7.81 (2H, d, J=8 Hz).

PREPARATION 3

The following compounds were prepared according to similar manners to those of Preparations 1 and 2.

(1) (rac)-1-O-Hexyl-2-O-methoxycarbonyl-3-O-trityl-glycerol (oil).

I.R. (film): 3050, 2950, 2920, 1745, 1270 cm$^{-1}$.

N.M.R. (CCl$_4$)ppm 0.87 (3H, m), 1.05~1.65 (8H, m), 3.25~3.82 (6H, m), 3.72 (3H, s), 4.87 (1H, m), 7.25 (15H, m).

(2) (rac) 1-O-Octyl-2-O-methoxycarbonyl-3-O-trityl-glycerol (colorless oil).

I.R. (film): 2920, 2850, 1745, 1270 cm$^{-1}$.

N.M.R. (CCl$_4$)ppm 0.90 (3H, t, J=5 Hz), 1.08~1.67 (12H, m), 3.17~3.80 (6H, m), 3.88 (3H, s), 4.87 (1H, m), 7.30 (15H, m).

(3) (rac)-1-O-Decyl-2-O-methoxycarbonyl-3-O-trityl-glycerol (oil).

I.R. (film): 3000, 1750, 1595 cm$^{-1}$.

N.M.R. (CDCl$_3$)ppm 0.90 (3H, t, J=5 Hz), 1.0~1.6 (16H, m), 3.2~3.7 (6H, m), 3.76 (3H, s), 5.00 (1H, m), 7.25 (15H, m).

(4) (rac)-1-O-Dodecyl-2-O-ethoxycarbonyl-3-O-trityl-glycerol (colorless oil).

I.R. (film): 2900, 2840, 1740, 1255 cm$^{-1}$.

N.M.R. (CCl$_4$)ppm 0.88 (3H, t, J=5 Hz), 1.02~1.70 (23H, m), 3.20~3.52 (6H, m), 4.12 (2H, q, J=7 Hz), 4.83 (1H, m), 7.25 (15H, m).

(5) (rac)-1-O-Tetradecyl-2-O-methoxycarbonyl-3-O-trityl-glycerol (colorless oil).

I.R. (film): 2920, 2850, 1745, 1265 cm$^{-1}$.

N.M.R. (CDCl$_3$)ppm 0.70~1.70 (27H, m), 3.37 (2 H, t, J=4.0 Hz), 3.20~3.50 (2H, m), 3.65 (2H, d, J=6.0 Hz), 3.80 (3H, s), 5.05 (1H, m), 7.4 (15H, m).

(6) (rac)-1-O-Hexadecyl-2-O-methoxycarbonyl-glycerol-3-tosylate.

m.p. 46° to 49° C.

I.R. (nujol): 1750, 1260, 1175 cm$^{-1}$.

N.M.R. (CDCl$_3$)ppm 0.88 (3H, t, J=5 Hz), 1.00~1.60 (28H, m), 2.45 (3H, s), 3.40 (2H, t, J=5.5 Hz), 3.55 (2H, d, J=6 Hz), 3.75 (3H, s), 4.15 (2H, m), 4.90 (1H, m), 7.35 (2H, d, J=8 Hz), 7.81 (2H, d, J=8 Hz).

(7) (rac)-1-O-Octadecyl-2O-methoxycarbonyl-3-O-trityl-glycerol.

m.p. 63° to 64° C.

I.R. (nujol): 1740, 1265 cm$^{-1}$.

N.M.R. (CDCl$_3$)ppm 0.86 (3H, t, J=6 Hz), 1.06~1.83 (32H, m), 3.30 (2H, d, J=5 Hz), 3.41 (2H, t, J=6 Hz), 3.63 (2H, d, J=5 Hz), 3.76 (3H, s), 5.03 (1H, m), 7.39 (15H, m).

(8) (rac)-1-O-Octadecyl-2-O-propoxycarbonyl-3-O-trityl-glycerol (colorless oil).

I.R. (film): 2920, 2850, 1740, 1255 cm$^{-1}$.

N.M.R. (CDCl$_3$)ppm 0.7~2.1 (40H, m), 3.2~3.55 (2H, m), 3.33 (2H, t, J=4.0 Hz), 3.63 (2H, d, J=5.0 Hz), 4.13 (2H, t, J=6.5 Hz), 5.03 (1H, m), 7.40 (15H, m).

(9) (rac)-1-O-Octadecyl-2-O-isopropoxycarbonyl-3-O-trityl-glycerol (colorless oil).

I.R. (film): 3050, 3025, 1740 cm$^{-1}$.

N.M.R. (CDCl$_3$)ppm 0.90 (3H, t, J=5 Hz), 1.10~1.60 (38H, m), 3.30~3.60 (6H, m), 4.70~5.30 (2H, m), 7.30 (15H, m).

(10) (rac)-1-O-Octadecyl-2-O-isobutoxycarbonyl-3-O-trityl-glycerol (colorless oil).

I.R. (film): 2920, 2850, 1745, 1250 cm$^{-1}$.

N.M.R. (CCl$_4$)ppm 0.60~1.46 (41H, m), 1.83 (1H, m), 3.00~3.73 (8H, m), 4.86 (1H, m), 7.03 (15H, m).

(11) (rac)-1-O-Octadecyl-2-O-butoxycarbonyl-3-O-trityl-glycerol.

m.p. 68° C.

I.R. (nujol): 1745, 1590 cm$^{-1}$.

N.M.R. (CDCl$_3$)ppm 0.80~1.80 (42H, m), 3.31 (2H, d, J=5 Hz), 3.41 (2H, t, J=6 Hz), 3.63 (2H, d, J=5 Hz), 4.16 (2H, t, J=6 Hz), 5.05 (1H, m), 7.36 (15H, m).

(12) (rac)-1-O-Octadecyl-2-O-benzyloxycarbonyl-3-O-trityl-glycerol (colorless oil).

I.R. (film): 2920, 2850, 1740, 1250 cm$^{-1}$.

N.M.R. (CDCl$_3$)ppm 0.70~1.70 (35H, m), 3.10~3.50 (4H, m), 3.60 (2H, d, J=4.0 Hz), 5.05 (1H, m), 5.16 (2H, s), 7.30 (20H, m).

(13) (rac)-1-O-Trityl-2-O-methoxycarbonyl-1,2-butanediol m.p. 95° C.

I.R. (nujol): 1740 cm$^{-1}$.

N.M.R. (CDCl$_3$)ppm 0.83 (3H, t, J=7 Hz), 1.68 (2H, m), 3.20 (2H, d, J=6 Hz), 3.78 (3H, s), 4.86 (1H, m), 7.36 (15H, m).

(14) (rac)-1-O-Trityl-2-O-methoxycarbonyl-1,2-octadecanediol.

I.R. (nujol): 1745, 1440, 1265 cm$^{-1}$.

N.M.R. (100 MHz, CCl$_4$)ppm 0.87 (3H, m), 1.26 (28H, s), 1.53 (2H, m), 3.08 (2H, d, J=5.5 Hz) 3.70 (3H, s), 4.75 (1H, m), 7.24 (15H, m).

(15) (rac)-1-s-Octadecyl-2-O-methoxycarbonyl-3-O-trityl-thioglycerol (colorless oil).

I.R. (film): 2930, 2850, 1745, 1595 cm$^{-1}$.

N.M.R. (CCl$_4$)ppm 0.83~1.58 (35H, m), 2.45 (2H, t, J=7 Hz), 2.71 (2H, d, J=7 Hz), 3.28 (2H, d, J=5 Hz), 3.75 (3H, s), 4.98 (1H, m), 7.26 (15H, m).

(16) (rac)-1-O-Benzyl-2-O-methoxycarbonyl-3-O-trityl-glycerol (oil).

I.R. (film): 3000, 1740 cm$^{-1}$.

N.M.R. (CDCl$_3$)ppm 3.33 (2H, d, J=4.5 Hz), 3.70 (2H, d, J=4.5 Hz), 3.73 (3H, s), 4.51 (2H, s), 4.95 (1H, m), 7.1~7.4 (20H, m).

(17) (rac)-1-O-Trityl-2-O-methoxycarbonyl-3-octadecanoylamino-1,2-propanediol (colorless oil).

I.R. (film): 3280, 2950, 2850, 1745, 1260 cm$^{-1}$.

N.M.R. (CDCl$_3$)ppm 0.88 (3H, t, J=6 Hz), 1.06~1.66 (30H, m), 2.06 (2H, t, J=6 Hz), 3.21~3.76 (4H, m), 3.80 (3H, s), 4.95 (1H, m), 5.70 (1H, t, J=6 Hz), 7.36 (15H, m).

PREPARATION 4

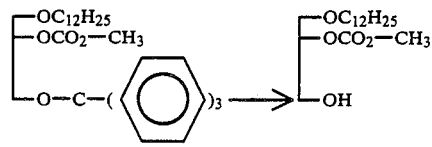

To a solution of (rac)-1-O-dodecyl-2-O-methoxycarbonyl-3-O-trityl-glycerol (10.2 g) in methylene chloride (100 ml) was added trifluoroacetic acid (10 ml) in one portion. After the yellow solution was stirred for 8 minutes at ambient temperature, ice water (100 ml) was added. The organic layer was washed with aqueous sodium bicarbonate solution and water, dried, and evaporated under reduced pressure. The residue was treated with n-hexane (50 ml) to remove triphenylmethanol as a white crystal. The filtrate was evaporated to give 6.22 g of (rac)-1-O-dodecyl-2-O-methoxycarbonyl-glycerol as a colorless oil (unstable oil).

I.R. (film): 3450, 1745 cm$^{-1}$.

N.M.R. (CDCl$_3$)ppm 0.91 (3H, t, J=5 Hz), 1.08 1.83 (20H, m), 2.96 (1H, s), 3.50 (2H, t, J=6 Hz), 3.66 (2H, d, J=5 Hz), 3.83 (3H, s), 3.86 (2H, d, J=5 Hz), 4.91 (1H, m).

PREPARATION 5

The following compounds are prepared according to the similar manner to that of Preparation 4.

(1) (rac)-1-O-Hexyl-2-O-methoxycarbonyl-glycerol (oil).
  I.R. (film): 3450, 2950, 2750, 1755, 1270 cm$^{-1}$.
(2) (rac)-1-O-Octyl-2-Omethoxycarbonyl-glycerol (oil).
  I.R. (film): 3450, 2900, 2850, 1750, 1265 cm$^{-1}$.
(3) (rac)-1-O-Decyl-2-O-methoxycarbonyl-glycerol (oil).
  I.R. (film): 3450, 1750 cm$^{-1}$.
(4) (rac)-1-O-Dodecyl-2-O-ethoxycarbonyl-glycerol (oil).
  I.R. (film): 3450, 2900, 2800, 1740, 1260 cm$^{-1}$.
(5) (rac)-1-O-Tetradecyl-2-O-methoxycarbonyl-glycerol (colorless oil).
  I.R. (film): 3450, 2920. 2850 cm$^{-1}$.
(6) (rac)-1-O-Octadecyl-2-O-methoxycarbonyl-glycerol.
  m.p. 43° to 47° C.
  I.R. (nujol): 3300, 1740 cm$^{-1}$.
(7) (rac)-1-O-Octadecyl-2-O-propoxycarbonyl-glycerol (colorless oil).
  I.R. (film): 3450, 2900, 2850, 1740, 1255 cm$^{-1}$.
(8) (rac)-1-O-Octadecyl-2-O-isopropoxycarbonyl-glycerol.
  I.R. (CHCl$_3$): 3450, 1740 cm$^{-1}$.
(9) (rac)-1-O-Octadecyl-2-O-isobutoxycarbonyl-glycerol (colorless oil).
  I.R. (film): 3450, 2920, 2850, 1745, 1300 cm$^{-1}$.
(10) (rac)-1-O-Octadecyl-2-O-butoxycarbonyl-glycerol (colorless oil).
  I.R. (film): 3450, 2920, 2850, 1740 cm$^{-1}$.
(11) (rac)-1-O-Octadecyl-2-O-benzyloxycarbonyl-glycerol (colorless oil).
  I.R. (film): 3450, 2920, 2850, 1745, 1260 cm$^{-1}$.
(12) (rac)-2-O-Methoxycarbonyl-1,2-butanediol (colorless oil).
  I.R. (film): 3450, 1740 cm$^{-1}$.
(13) (rac)-2-O-Methoxycarbonyl-1,2-octadecanediol.
  m.p. 66° to 67° C.
  I.R. (KBr): 3300, 2900, 2850, 1735, 1260 cm$^{-1}$.
  N.M.R. (CDCl$_3$) ppm 0.88 (3H, m), 1.26 (28H, s), 2.05 (2H, m), 3.87 (5H, s), 4.75 (1H, m).
(14) (rac)-1-s-Octadecyl-2-O-methoxycarbonyl-thioglycerol (thick oil).
  I.R. (nujol): 3300, 1740, 1265 cm$^{-1}$.
(15) (rac)-1-O-Benzyl-2-O-Benzyl-2-O-methoxycarbonyl-glycerol
  I.R. (neat): 3450, 1740 cm$^{-1}$.
(16) (rac)-2-O-Methoxycarbonyl-3-octadecanoylamino-1,2-propanediol.
  m.p. 61° C.
  I.R. (Nujol): 3300, 3250, 1740, 1635 cm$^{-1}$.

PREPARATION 6

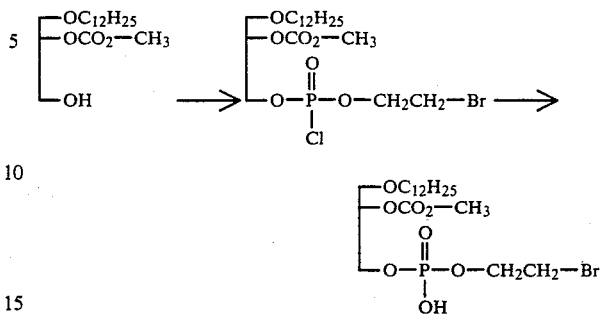

To a solution of 2-bromoethyldichlorophosphate (4.59 g) in dry chloroform (6 ml) was added, dropwise over 20 minutes, a solution of (rac)-1-O-dodecyl-2-O-methoxycarbonyl-glycerol (5.77 g) and triethylamine (1.92 g) in dry chloroform (6 ml) at 0° to 5° C. After the addition was completed, the mixture was allowed to warm to ambient temperature, stirred for 2 hours, and then cooled in an ice bath.

To the resultant thick solution containing (rac)-1-O-dodecyl-2-O-methoxycarbonyl-glycerol-3-(2-bromoethyl)-chlorophosphate was added dropwise a mixture of water (5 ml) and pyridine (10 ml) below 15° C. The resulting solution was allowed to warm to ambient temperature followed by stirring for 30 minutes. The solvents were then evaporated under reduced pressure. The residue was dissolved in aqueous sodium bicarbonate solution and diethyl ether. The aqueous phase was washed with diethyl ether, adjusted to pH 1 with 10% hydrochloric acid, and extracted twice with diethyl ether—ethyl acetate (50%).

The organic layer was washed with water, dried, and evaporated under reduced pressure to yield 5.17 g of (rac)-1-O-dodecyl-2-O-methoxycarbonyl-glycerol-3-(2-bromoethyl)phosphate (thick oil).

I.R. (film): 3500, 1745, 1270 cm$^{-1}$.

PREPARATION 7

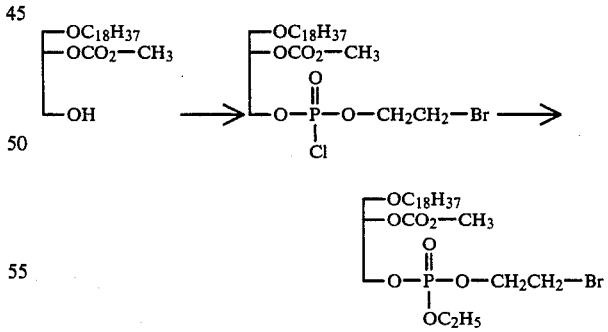

To a stirred solution of 2-bromoethyldichlorophosphate (4.35 g) in dry chloroform (6 ml) was added, dropwise over 30 minutes, a solution of (rac)-1-O-octadecyl-2-O-methoxycarbonyl-glycerol (7.23 g) and triethylamine (1.82 g) in dry chloroform (10 ml) in an ice bath. After the addition, the reaction mixture was allowed to warm to ambient temperature and stirred for 2 hours.

The mixture containing (rac)-1-O-octadecyl-2-O-methoxycarbonyl-glycerol-3-(2-bromoethyl)chlorophosphate was again cooled to 5° C. and a mixture of ethanol (4.5 ml) and dry pyridine (9 ml) was added dropwise over 20 minutes. After stirring for 30 minutes at 5° C. and for 1 hour at ambient temperature, the reaction mixture was washed with aqueous hydrochloric acid and brine, dried, and evaporated under reduced pressure. The obtained residue was purified by column chromatography on silica gel (200 g, elution by benzene, benzene/chloroform=1/1, and chloroform) to yield 5.76 g of (rac)-1-O-octadecyl-2-O-methoxycarbonyl-glycerol-3-(2-bromoethyl ethyl)phosphate as a thick oil.

I.R. (film): 3470, 1750, 1265 cm$^{-1}$.

PREPARATION 8

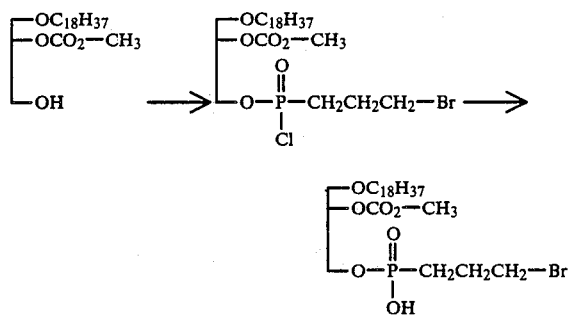

To a solution of 3-bromopropyldichlorophosphonate (3.41 g) in dry chloroform (5.5 ml) was added, dropwise over 40 minutes, a solution of (rac)-1-O-octadecyl-2-O-methoxycarbonyl-glycerol (5.20 g) and triethylamine (1.44 g) in dry chloroform (6.5 ml) at 0° to 5° C. After the addition was completed, an ice bath was removed and the stirring was continued for 2.5 hours. The mixture containing (rac)-1-O-octadecyl-2-O-methoxycarbonyl-glycerol-3-(3-bromopropyl)chlorophosphonate was cooled to 5° C. and a mixture of water (4 ml) and pyridine (8 ml) was added dropwise below 10° C. The resulting mixture was stirred for 30 minutes at ambient temperature and then evaporated under reduced pressure. The residue dissolved in ethyl acetate (200 ml) was washed with aqueous hydrochloric acid and water, dried, and evaporated. The residue (7.23 g) was chromatographed on silica gel (72 g, elution by chloroform) to yield 4.27 g of (rac)-1-O-octadecyl-2-O-methoxycarbonyl-glycerol-3-(3-bromopropyl)phosphonate.

I.R. (film): 1750, 1460, 1440, 1265 cm$^{-1}$.

PREPARATION 9

The following compounds were prepared according to the similar manners to those of Preparations 6, 7 and 8.

(1) (rac)-1-O-Hexyl-2-O-methoxycarbonyl-glycerol-3-(2-bromoethyl)phosphate (oil).
I.R. (film): 2950, 2910, 1750, 1270 cm$^{-1}$.
(2) (rac)-1-O-Octyl-2-O-methoxycarbonyl-glycerol-3-(2-bromoethyl)phosphate (oil).
I.R. (film): 2950, 2900, 1750, 1260, 1020 cm$^{-1}$.
(3) (rac)-1-O-Decyl-2-O-methoxycarbonyl-glycerol-3-(2-bromoethyl)phosphate (thick oil).
I.R. (film): 3500, 1745, 1270 cm$^{-1}$.
(4) (rac)-1-O-Dodecyl-2-O-ethoxycarbonyl-glycerol-3-(2-bromoethyl)phosphate (thick oil).
I.R. (film): 2900, 2850, 1745, 1250 cm$^{-1}$.
(5) (rac)-1-O-Tetradecyl-2-O-methoxycarbonyl-glycerol-3-(2-bromoethyl)phosphate (colorless oil).
I.R. (film): 2920, 2850, 1750, 1270, 1120, 1070, 1020 cm$^{-1}$.
(6) (rac)-1-O-Octadecyl-2-O-methoxycarbonyl-glycerol-3-(2-bromoethyl)phosphate (oil).
I.R. (nujol): 1750, 1265 cm$^{-1}$.
(7) (rac)-1-O-Octadecyl-2-O-propoxycarbonyl-glycerol-3-(2-bromoethyl)phosphate (pale yellow oil).
I.R. (film): 2920, 2850, 1740, 1250, 1120, 1070 cm$^{-1}$.
(8) (rac)-1-O-Octadecyl-2-O-isopropoxycarbonyl-glycerol-3-(2-bromoethyl)phosphate (thick oil).
I.R. (film): 3500, 1740, 1260 cm$^{-1}$.
(9) (rac)-1-O-Octadecyl-2-O-isobutoxycarbonyl-glycerol-3-(2-bromoethyl)phosphate (pale yellow oil).
I.R. (film): 2920, 2850, 1745, 1250, 1070 cm$^{-1}$.
(10) (rac)-1-O-Octadecyl-2-O-butoxycarbonyl-glycerol-3-(2-bromoethyl)phosphate (colorless oil).
I.R. (film): 2930, 2840, 1740, 1255 cm$^{-1}$.
(11) (rac)-1-O-Octadecyl-2-O-benzyloxycarbonyl-glycerol-3-(2-bromoethyl)phosphate (pale yellow oil).
I.R. (film): 2920, 2850, 1740, 1250, 1110, 1075 cm$^{-1}$.
(12) (rac)-2-O-Methoxycarbonyl-1,2-butanediol-1-(2-bromoethyl)phosphate (yellow oil).
I.R. (film): 1740, 1250 cm$^{-1}$.
(13) (rac)-2-O-Methoxycarbonyl-1,2-octadecanediol-1-(2-bromoethyl)phosphate.
I.R. (neat): 2900, 2840, 1750, 1460, 1440, 1265 cm$^{-1}$.
N.M.R. (CDCl$_3$) ppm 0.86 (3H, m), 1.27 (30H, s) 3.4~4.4 (9H, m), 4.87 (1H, m).
(14) (rac)-1-s-Octadecyl-2-O-methoxycarbonyl-thio-glycerol-3-(2-bromoethyl)phosphate (thick oil).
I.R. (film): 2920, 2850, 1745, 1265 cm$^{-1}$.
(15) (rac)-1-O-Benzyl-2-O-methoxycarbonyl-glycerol-3-(2-bromoethyl)phosphate.
I.R. (nujol): 1745, 1450 cm$^{-1}$.
(16) (rac)-2-O-Methoxycarbonyl-3-octadecanoylamino-1,2-propanediol-1-(2-bromoethyl)phosphate.
m.p. 128° to 134° C.
I.R. (nujol): 3300, 1745, 1645, 1260 cm$^{-1}$.

PREPARATION 10

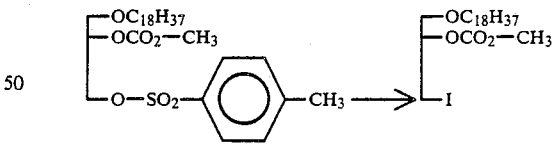

A mixture of (rac)-1-O-Octadecyl-2-O-methoxycarbonyl-glycerol-3-tosylate (3.25 g), sodium iodide (1.8 g), and dry acetone (32 ml) was stirred for 3 hours at ambient temperature in the dark and then refluxed for 16 hours. After the mixture was cooled to ambient temperature, the precipitate was filtered followed by washing with acetone. The filtrate was evaporated under reduced pressure. The oily residue was purified by chromatography on silica gel (40 g, elution by benzene) to give 1.97 g of (rac)-1-O-Octadecyl-2-O-methoxycarbonyl-glycerol-iodohydrin as a colorless oil, which was crystallized from methanol to yield 1.67 g of a white solid.
m.p. 41° to 43.5° C.
I.R. (nujol): 1750, 1460, 1290, 1265 cm$^{-1}$.

N.M.R. (CDCl$_3$)ppm 0.8~1.83 (35H, m), 3.38~3.93 (6H, m), 3.83 (3H, s), 4.76 (1H, m).

PREPARATION 11

The following compound was prepared according to the similar manner to that of Preparation 10.
(1) (rac)-1-O-Hexadecyl-2-O-methoxycarbonyl-glycerol-iodohydrin.
m.p. 37° to 40° C.
I.R. (nujol): 1750, 1460, 1290, 1265 cm$^{-1}$.
N.M.R. (CDCl$_3$)ppm 0.88 (3H, t, J=5 Hz), 1.0~1.60 (28H, m), 3.30~3.70 (6H, m), 3.82 (3H, s), 4.7 (1H, m).

PREPARATION 12

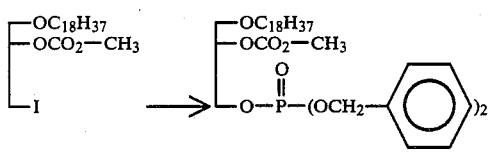

A mixture of (rac)-1-O-Octadecyl-2-O-methoxycarbonyl-glycerol-iodohydrin (18.0 g), silver salt of dibenzylphosphate (14.9 g), and dry xylene (360 ml) was refluxed for 40 minutes in the dark. After being chilled, the mixture was filtered. The filtrate was twice washed with 5% aqueous potassium bicarbonate solution and water, dried, and evaporated under reduced pressure. The crude oil was purified by chromatography on silica gel (160 g, elution by chloroform) to yield 21.2 g of (rac)-1-O-octadecyl-2-O-methoxycarbonyl-glycerol-3-(dibenzyl)phosphate as a pale yellow oil.
I.R. (CHCl$_3$): 1745, 1440, 1270, 1110 cm$^{-1}$.
N.M.R. (CCl$_4$)ppm 0.86~1.66 (35H, m), 3.33~3.83 (5H, m), 3.76 (3H, s), 4.11 (2H, m), 5.01 (4H, d, J=8 Hz), 7.33 (10H, s).

PREPARATION 13

The following compound was prepared according to the similar manner to that of Preparation 12. (rac)-1-O-Hexadecyl-2-O-methoxycarbonyl-glycerol-3-(dibenzyl)phosphate (oil).
I.R. (film): 1750, 1450, 1270, 1020 cm$^{-1}$.
N.M.R. (CDCl$_3$)ppm 0.9~1.6 (31H, m), 3.4~3.6 (4H, m), 3.77 (3H, s), 4.1~4.3 (2H, m), 5.08 (4H, d, J=8 Hz), 5.10 (1H, m), 7.37 (10H, s).

PREPARATION 14

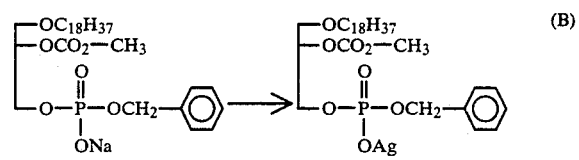

A mixture of (rac)-1-O-Octadecyl-2-O-methoxycarbonylglycerol-3-(dibenzyl)phosphate (18.7 g), sodium iodide (8.46 g), and dry acetone (230 ml) was refluxed for 8.5 hours. After being cooled in an ice bath, the precipitate was rapidly collected by filtration, washed with cooled acetone, and then dissolved in methanol (20 ml). The solution was concentrated to dryness to give 13.8 g of sodium salt of (rac)-1-O-octadecyl-2-O-methoxycarbonyl-glycerol-3-(benzyl)phosphate, which was used to the next step without further purification.

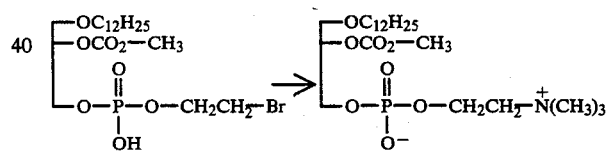

To a warmed solution of sodium salt of (rac)-1-O-octadecyl-2-O-methoxycarbonyl-glycerol-3-(benzyl)phosphate (13.83 g) in water (100 ml) was added a solution of silver nitrate (3.96 g) in water (5 ml) in one portion. After standing for 20 minutes, the precipitate was collected by filtration, washed with water, and dried over phosphorus pentoxide in the dark under reduced pressure to yield 12.2 g of silver salt of (rac)-1-O-octadecyl-2-O-methoxycarbonyl-glycerol-3-(benzyl)phosphate (12.2 g) as a white solid.

PREPARATION 15

The following compounds (1) (A) and (1) (B) were prepared according to the similar manners to those of Preparation 14 (A) and Preparation 14 (B), respectively.
(1) (A) Sodium salt of (rac)-1-O-hexadecyl-2-O-methoxycarbonyl-glycerol-3-(benzyl)phosphate.
(1) (B) Silver salt of (rac)-1-O-hexadecyl-2-O-methoxycarbonyl-glycerol-3-(benzyl)phosphate.
m.p. 76° to 80° C.
I.R. (nujol): 1740, 1260, 1190, 1070 cm$^{-1}$.
N.M.R. (CDCl$_3$)ppm 0.88 (3H, t, J=5 Hz), 1.0~1.7 (28H, m), 3.2~3.6 (4H, m), 3.72 (3H, s), 3.8~4.2 (2H, m), 4.7~5.2 (3H, m), 7.2~7.6 (5H, m).

EXAMPLE 1

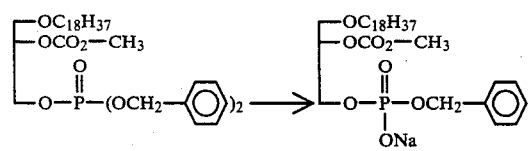

A mixture of (rac)-1-O-dodecyl-2-O-methoxycarbonyl-glycerol-3-(2-bromoethyl)phosphate (5.10 g), aqueous trimethylamine solution (16.8 g, 35%), and methanol (51 ml) was heated for 15 hours at 50° C. The solvents were then evaporated to dryness. The residue was three times washed with acetone, dissolved in 90% aqueous methanol (40 ml), and treated with silver acetate (3.32 g) for 45 minutes at ambient temperature. The mixture was filterd and the filtrate was evaporated to dryness. The residue was chromatographed on silica gel (150 g, elution by chloroform:methanol:water, 65:25:4, v/v/v). The obtained solid was recrystallized from chloroform-acetone to yield 1.3 g of (rac)-1-O-dodecyl-2-O-methoxycarbonyl-glycerol-3-phosphorylcholine.
m.p. 223° C. (dec.).
I.R. (nujol): 3350, 1740, 1260 cm$^{-1}$.
N.M.R. (CD$_3$OD)ppm 0.89 (3H, t, J=6 Hz), 1.06~1.70 (20H, m), 3.08~4.26 (10H, m), 3.24 (9H, s), 3.77 (3H, s), 4.97 (1H, m).
Anal. Calcd. for C$_{22}$H$_{46}$O$_8$NP.1½ H$_2$O. C: 51.21, H: 9.67, N: 2.74. Found: C: 51.46, H: 9.41, N: 2.65.

EXAMPLE 2

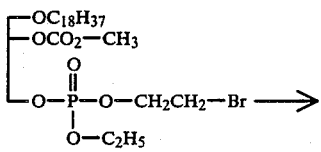

A solution of (rac)-1-O-octadecyl-2-O-methoxycarbonyl-glycerol-3-(2-bromoethyl ethyl)phosphate (5.70 g) and trimethylamine (30 ml, 4N-tetrahydrofuran solution) in dry tetrahydrofuran (50 ml) was stirred for 3 hours at ambient temperature and then for 9 hours at 50° C. The resulting mixture was evaporated under reduced pressure. The obtained residue was pulverized with acetone. The crude solid was chromatographed on silica gel (120 g, elution by chloroform:methanol:water, 64:25:4) to yield bromide salt (2.4 g) of (rac)-1-O-octadecyl-2-O-methoxycarbonyl-glycerol-3-(ethyl 2-trimethylammonioethyl)phosphate, which was recrystallized from acetone. (yield 1.78 g).

m.p. 135° C.

I.R. (nujol): 3400, 1750, 1260 cm$^{-1}$.

N.M.R. (CDCl$_3$)ppm 0.88~1.76 (38H, m), 3.39~4.56 (12H, m), 3.58 (9H, s), 3.82 (3H, s), 4.98 (1H, m).

Anal. Calcd. for C$_{30}$H$_{63}$O$_8$NPBr.½H$_2$O. C: 52.54, H: 9.41, N: 2.04. Found: C: 52.89, H: 9.44, N: 1.93.

EXAMPLE 3

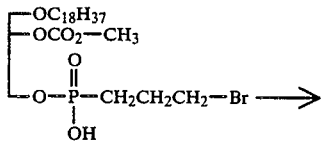

A mixture of (rac)-1-O-octadecyl-2-O-methoxycarbonyl-glycerol-3-(3-bromopropyl)phosphonate (4.27 g), trimethylamine (ca 25% in tetrahydrofuran, 17 ml), and dry tetrahydrofuran (36 ml) was stirred for 2 hours at ambient temperature and then for 18.5 hours at 50° C. The solvent was removed under reduced pressure. The residue was triturated in acetone and collected by filtration. The crude solid dissolved in 90% aqueous methanol (50 ml) was treated with silver acetate (1.87 g) for 1 hour at ambient temperature. The precipitates were filtered off and washed with methanol. The filtrate and washings were combined and evaporated to dryness. The residue (3.99 g) was purified by chromatography on silica gel (120 g, elution by a mixture of chloroform, methanol and water, 65:25:4) to give 2.25 g of the object compound, which was recrystallized from chloroform-acetone to yield 1.49 g of (rac)-1-O-octadecyl-2-O-methoxycarbonyl-glycerol-3-(3-trimethylammoniopropyl)phosphonate as a white solid. m.p. 220° C. (dec.)

I.R. (nujol): 3300, 1740, 1265, 1200, 1050 cm$^{-1}$.

N.M.R. (CD$_3$OD)ppm 0.7~2.2 (35H, m), 3.12 (9H, s), 3.2~3.54 (6H, m), 3.6 (2H, d, J=6.0 Hz), 3.74 (3H, s), 3.9~4.1 (2H, m), 4.9~5.0 (1H, m).

Anal. Calcd for C$_{29}$H$_{60}$NO$_7$P.H$_2$O. C: 59.67, H: 10.70, N: 2.40. Found: C: 59.08, H: 11.07, N: 2.30.

EXAMPLE 4

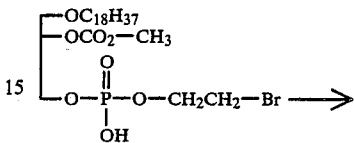

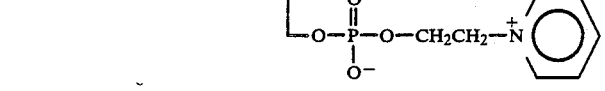

A solution of (rac)-1-O-octadecyl-2-O-methoxycarbonylglycerol-3-(2-bromoethyl)phosphate (4.0 g) in dry pyridine (20 ml) was heated with stirring for 1.5 hours at 60° C., and then evaporated under reduced pressure. The residue, dissolved in 90% aqueous methanol (50 ml), was treated with silver acetate (2.27 g) for 30 minutes at ambient temperature. The precipitate was filtered and washed with methanol. The combined filtrates were evaporated to dryness. The residue was purified by columnchromatography on silica gel (100 g, elution by chloroform:methanol:water, 65:25:4) to give 2.98 g of (rac)-1-O-octadecyl-2-O-methoxycarbonyl-glycerol-3-(2-pyridinioethyl)phosphate as a white solid, which was recrystallized from chloroform-acetone, yield 2.50 g.

m.p. 166° C. (dec.).

I.R. (nujol): 3370, 1755 (shoulder), 1735, 1235 cm$^{-1}$.

N.M.R. (CD$_3$OD)ppm 0.91 (3H, t, J=7 Hz), 1.06~1.80 (32H, m), 3.40~3.99 (8H, m), 4.32 (2H, m), 3.78 (3H, s), 4.90 (1H, m), 8.06~9.09 (5H, m).

Anal. Calcd. for C$_{30}$H$_{54}$O$_8$NP.H$_2$O. C: 59.48, H: 9.31, N: 2.31. Found: C: 59.24, H: 9.40, N: 2.47.

EXAMPLE 5

The following compounds were prepared according to the similar manners to those of Examples 1 to 4.

(1) (rac)-1-O-Hexyl-2-O-methoxycarbonyl-glycerol-3-phosphorylcholine (oil).

I.R. (CHCl$_3$): 3300, 2900, 2850, 1740, 1270 cm$^{-1}$.

N.M.R. (CD$_3$OD)ppm 0.89 (3H, m), 1.08~1.68 (8H, m), 3.26 (9H, s), 3.47~4.01 (10H, m), 3.79 (3H, s), 4.97 (1H, m).

(2) (rac)-1-O-Octyl-2-O-methoxycarbonyl-glycerol-3-phosphorylcholine.

m.p. 213° to 216° C.

I.R. (nujol): 3400, 1750, 1250 cm$^{-1}$.

N.M.R. (CD$_3$OD)ppm 0.90 (3H, t, J=6 Hz), 1.08~1.69 (12H, m), 3.26 (9H, s), 3.47~4.12 (10H, m), 3.79 (3H, s), 4.97 (1H, m).

Anal. Calcd. for C$_{18}$H$_{38}$NO$_8$P.H$_2$O. C: 48.53, H: 9.05, N: 3.14. Found: C: 48.62, H: 9.31, N: 3.09.

(3) (rac)-1-O-Decyl-2-O-methoxycarbonyl-glycerol-3-phosphorylcholine.

m.p. 230° C. (dec.)
I.R. (nujol): 3360, 1730, 1260 cm$^{-1}$.
N.M.R. (CD$_3$OD)ppm 0.9 (3H, t, J=5 Hz), 1.1~1.7 (16H, m), 3.25 (9H, s), 3.4~4.5 (10H, m), 3.77 (3H, s), 5.00 (1H, m).
Anal. Calcd. for C$_{20}$H$_{42}$NO$_8$P.H$_2$O. C: 50.73, H: 9.37, N: 2.96. Found: C: 50.25, H: 9.64, N: 2.73.

(4) (rac)-1-O-Decyl-2-O-methoxycarbonyl-glycerol-3-phosphoryl-(N-methyl)ethanolamine.
m.p. 175° C.
I.R. (CHCl$_3$): 3350, 2900, 2850, 1740, 1270 cm$^{-1}$.

(5) (rac)-1-O-Dodecyl-2-O-ethoxycarbonyl-glycerol-3-phosphorylcholine.
m.p. 220° C. (dec.).
I.R. (CHCl$_3$): 3300, 1740, 1260 cm$^{-1}$.
N.M.R. (CD$_3$OD)ppm 0.90 (3H, t, J=5 Hz), 1.10~1.71 (23H, m), 3.28 (9H, s), 3.31~4.40 (12H, m), 5.00 (1H, m).
Anal. Calcd. for C$_{23}$H$_{48}$NO$_8$P.H$_2$O. C: 53.58, H: 9.77, N: 2.72. Found: C: 53.52, H: 10.15, N: 2.74.

(6) (rac)-1-O-Tetradecyl-2-O-methoxycarbonyl-glycerol-3-phosphorylcholine.
m.p. 203° C. (dec.).
I.R. (nujol): 3380, 1745, 1265 cm$^{-1}$.
N.M.R. (CD$_3$OD)ppm 0.7~1.0 (3H, m), 1.0~1.7 (24H, m), 3.0~3.88 (6H, m), 3.22 (9H, s), 3.76 (3H, s), 3.88~4.4 (4H, m), 4.95 (1H, m).
Anal. Calcd. for C$_{24}$H$_{50}$O$_8$NP.2H$_2$O C: 52.63; H: 9.94, N: 2.55. Found: C: 53.06, H: 9.69, N: 2.36.

(7) (rac)-1-O-Hexadecyl-2-O-methoxycarbonyl-glycerol-3-phosphorylcholine.
m.p. 218° to 232° C. (dec.).
I.R. (nujol): 3390, 1740, 1100 cm$^{-1}$.

(8) (rac)-1-O-Octadecyl-2-O-methoxycarbonyl-glycerol-3-phosphorylcholine hygroscopic solid).
m.p. 275° C. (dec.).
I.R. (CHCl$_3$): 3400, 1745, 1630, 1090 cm$^{-1}$.

(9) (rac)-1-O-Octadecyl-2-O-methoxycarbonyl-glycerol-3-phosphorylethanolamine (white solid).
m.p. 196° to 200° C.
I.R. (nujol): 1740, 1270 cm$^{-1}$.

(10) (rac)-1-O-Octadecyl-2-O-ethoxycarbonyl-glycerol-3-phosphorylcholine (hygroscopic solid).
m.p. 220° C. (dec.).
I.R. (nujol): 3360, 1740, 1260, 1080, 1060 cm$^{-1}$.

(11) (rac)-1-O-Octadecyl-2-O-propoxycarbonyl-glycerol-3-phosphorylcholine.
m.p. 210° C. (dec.).
I.R. (nujol): 3380, 1740, 1250 cm$^{-1}$.
N.M.R. (CD$_3$OD)ppm 0.6~2.0 (40H, m), 3.24 (9H, s), 3.36~3.7 (6H, m), 3.8~4.4 (6H, m), 4.8~5.1 (1H, m).
Anal. Calcd. for C$_{30}$H$_{62}$O$_8$NP.2H$_2$O C: 57.03, H: 10.52, N: 2.22. Found: C: 57.49, H: 10.62, N: 2.41.

(12) (rac)-1-O-Octadecyl-2-O-isopropoxycarbonyl-glycerol-3-phosphorylcholine.
m.p. 240° C. (dec.).
I.R. (nujol): 3360, 1745, 1260 cm$^{-1}$.
N.M.R. (CD$_3$OD) ppm 0.90 (3H, t, J=5 Hz), 1.20~1.70 (38H, m), 3.25 (9H, s), 3.40~4.50 (11H, m), 5.00 (1H, m).
Anal. Calcd. for C$_{30}$H$_{62}$NO$_8$P.H$_2$O C: 58.70, H: 10.51, N: 2.28. Found: C: 58.04, H: 10.65, N: 2.06.

(13) (rac)-1-O-Octadecyl-2-O-isobutoxycarbonyl-glycerol-3-phosphorylcholine.
m.p. 213° to 215° C. (dec.).
I.R. (nujol): 3370, 1745, 1255 cm$^{-1}$.
N.M.R. (CD$_3$OD)ppm 0.70~1.70 (35H, m), 0.94 (6H, d, J=7 Hz), 1.91 (1H, m), 3.10~4.39 (12H, m), 3.19 (9H, s), 4.95 (1H, m).
Anal. Calcd. for C$_{31}$H$_{64}$O$_8$NP.H$_2$O C: 59.30, H: 10.59, N: 2.23. Found: C: 58.19, H: 10.23, N: 2.07.

(14) (rac)-1-O-Octadecyl-2-O-butoxycarbonyl-glycerol-3-phosphorylcholine.
m.p. 208° to 213° C. (dec.).
I.R. (nujol): 3470, 1745, 1255 cm$^{-1}$.
N.M.R. (CD$_3$OD)ppm 0.73~1.78 (42H, m), 3.09~4.38 (12H, m), 3.23 (9H, s), 4.96 (1H, m).
Anal. Calcd. for C$_{31}$H$_{64}$O$_8$NP.H$_2$O C: 59.30, H: 10.59, N: 2.23. Found: C: 58.33, H: 10.08, N: 2.29.

(15) (rac)-1-O-Octadecyl-2-O-benzyloxycarbonyl-glycerol-3-phosphorylcholine.
m.p. 172° C. (dec.).
I.R. (nujol): 3340, 1740, 1250 cm$^{-1}$.
N.M.R. (CD$_3$OD)ppm 0.7~1.8 (35H, m), 3.0~3.7 (6H, m), 3.14 (9H, s), 3.9~4.5 (4H, m), 4.9~5.2 (1H, m), 5.16 (2H, s), 7.35 (5H, m).
Anal. Calcd. for C$_{34}$H$_{62}$NO$_8$P.H$_2$O C: 61.70, H: 9.75, N: 2.12. Found: C: 61.62, H: 9.79, N: 2.07.

(16) (rac)-2-O-Methoxycarbonyl-1,2-butanediol-1-phosphorylcholine.
m.p. 98° to 102° C.
I.R. (nujol): 3370, 1735, 1270 cm$^{-1}$.
N.M.R. (CD$_3$OD)ppm 0.95 (3H, t, J=8 Hz), 1.64 (2H, m), 3.22 (9H, s), 3.66~3.91 (6H, m), 3.74 (3H, s), 4.69 (1H, m).
Anal. Calcd. for C$_{11}$H$_{24}$O$_7$NP.H$_2$O C: 39.88, H: 7.90, N: 4.22. Found: C: 39.49, H: 8.02, N: 4.51.

(17) (rac)-2-O-Methoxycarbonyl-1,2-octanedecanediol-1-phosphorylcholine.
m.p. 82° to 85° C.
I.R. (nujol): 3370, 1740, 1460, 1265 cm$^{-1}$.
N.M.R. (100 MHz, CDCl$_3$)ppm 0.89 (3H, m), 1.29 (28H, s), 1.55 (2H, m), 3.33 (9H, s), 3.78 (3H, s), 3.8 (4H, m), 4.3 (2H, m), 4.80 (1H, m).
Anal. Calcd. for C$_{25}$H$_{52}$O$_7$NP.H$_2$O C: 56.90, H: 10.32, N: 2.65. Found: C: 56.23, H: 10.34, N: 2.64.

(18) (rac)-1-S-Octadecyl-2-O-methoxycarbonyl-thio-glycerol-3-phosphorylcholine.
m.p. 210° to 214° C. (dec.)
I.R. (nujol): 3350, 1740, 1260 cm$^{-1}$.
N.M.R. (CD$_3$OD)ppm 0.88 (3H, t, J=6 Hz), 1.06~1.78 (32H, m), 2.56 (2H, t, J=7 Hz), 2.68~4.40 (8H, m), 3.21 (9H, s), 3.75 (3H, s), 4.86 (1H, m).
Anal. Calcd. for C$_{28}$H$_{58}$O$_7$NPS.H$_2$O C: 55.88, H: 10.05, N: 2.32. Found: C: 55.06, H: 9.96, N: 2.21.

(19) (rac)-1-O-Benzyl-2-O-methoxycarbonyl-glycerol-3-phosphorylcholine.
m.p. 69° to 70° C.
I.R. (nujol): 3370, 1745, 1450, 1265, 1085, 965 cm$^{-1}$.
N.M.R. (100 MHz, CDCl$_3$) ppm 3.24 (9H, s), 3.73 (3H, s), 3.66~4.13 (8H, m), 4.48 (2H, s), 4.98 (1H, m), 7.28 (5H, s).
Anal. Calcd. for C$_{17}$H$_{28}$O$_8$NP.H$_2$O C: 48.22, H: 7.14, N: 3.31. Found: C: 47.97, H: 7.24, N: 3.27.

(20) (rac)-2-O-Methoxycarbonyl-3-octadecanoylamino-1,2-propanediol-1-phosphorylcholine.
m.p. 220° C. (dec.).
I.R. (CHCl$_3$): 3300, 2900, 1745, 1260~1190 cm$^{-1}$.
N.M.R. (CD$_3$OD)ppm 0.89 (3H, t, J=5.5 Hz), 1.03~1.80 (30H, m), 2.18(2H, t, J=7 Hz), 3.22 (9H, s), 3.37~4.39 (8H, m), 3.75 (3H, s), 4.90 (1H, m).
Anal. Calcd. for C$_{28}$H$_{59}$N$_2$O$_9$P.1/2H$_2$O C: 55.19, H: 9.80, N: 4.52. Found: C: 55.34, H: 9.95, N: 4.69.

(21) (rac)-1-O-Decyl-2-O-methoxycarbonyl-glycerol-3-phosphorylethanolamine.
 m.p. 210° C. (dec.).
 I.R. (CHCl₃): 3250, 2900, 2850, 1740, 1265 cm⁻¹.
(22) (rac)-1-O-Decyl-2-O-methoxycarbonyl-glycerol-3-phosphoryl-(N-isopropyl)ethanolamine.
 m.p. 123° to 125° C.
 I.R. (nujol): 2700, 2530, 1745, 1260, 1230 cm⁻¹.

EXAMPLE 6

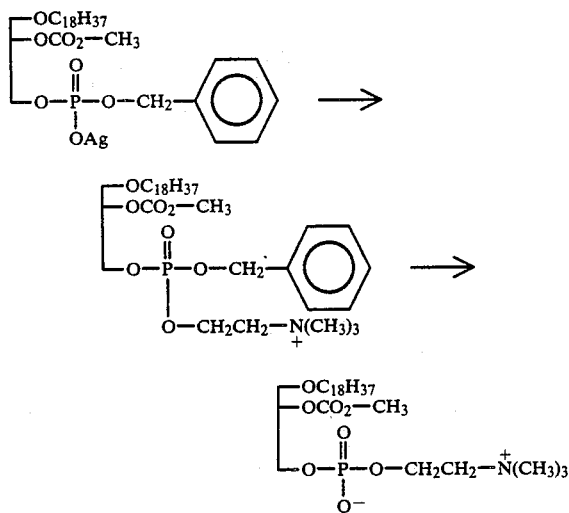

A magnetically stirred solution of silver salt of (rac)-1-O-octadecyl-2-O-methoxycarbonyl-glycerol-3-(benzyl)phosphate (8.16 g) and (2-bromoethyl)trimethylammonium picrate (9.48 g) in a mixed solvent of dry xylene (80 ml) and dry acetonitrile (40 ml) was refluxed for 3 hours in the dark. After cooling, the mixture was filtered. The filtrate was evaporated to dryness. The residue containing picrate salt of (rac)-1-O-octadecyl-2-O-methoxycarbonyl-glycerol-3-(benzyl 2-trimethylammonioethyl)phosphate was dissolved in dry acetone (150 ml) and anhydrous lithium bromide (3.60 g) was added thereto. The solution was refluxed for 4.5 hours and then evaporated under reduced pressure. The residue dissolved in a mixture of chloroform-methanol-water (1.5 l, 1:2:1, v/v/v) was passed through a mixed ion-exchange column, containing Amberlite IRC-50(H+) (24 g) and IR-45(OH−) (42 g). After washing the column with the solvent (1.5 l), the combined eluates were evaporated under reduced pressure. Purification of the residue was carried out by column chromatography on silica gel (480 g, elution by chloroform-methylalcohol-water, 65:25:4, v/v/v). The combined eluates containing the desired product were evaporated to dryness. The residue was crystallized from acetone and dried under reduced pressure. The crude solid was recrystallized from chloroform-acetone to yield 3.9 g of (rac)-1-O-octadecyl-2-O-methoxycarbonyl-glycerol-3-phosphorylcholine as a hygroscopic solid.
 m.p. 275° C. (dec.)
 I.R. (CHCl₃): 3400, 1745, 1630, 1090 cm⁻¹.
 N.M.R. (CD₃OD) ppm 0.92~1.70 (35H, m), 3.30 (9H, s), 3.80 (3H, s), 3.50~5.10 (1H, m).

EXAMPLE 7

The following compounds were prepared according to the similar manner to that of Example 6.

(1) (rac)-1-O-Hexyl-2-O-methoxycarbonyl-glycerol-3-phosphorylcholine (oil).
 I.R. (CHCl₃): 3300, 2900, 2850, 1740, 1270 cm⁻¹.
(2) (rac)-1-O-Octyl-2-O-methoxycarbonyl-glycerol-3-phosphorylcholine.
 m.p. 213° to 216° C.
 I.R. (nujol): 3400, 1750, 1250 cm⁻¹.
(3) (rac)-1-O-Decyl-2-O-methoxycarbonyl-glycerol-3-phosphorylcholine.
 m.p. 230° C. (dec.).
 I.R. (nujol): 3360, 1730, 1260 cm⁻¹.
(4) (rac)-1-O-Decyl-2-O-methoxycarbonyl-glycerol-3-phosphoryl-(N-methyl)ethanolamine.
 m.p. 175° C.
 I.R. (CHCl₃): 3350, 2900, 2850, 1740, 1270 cm⁻¹.
(5) (rac)-1-O-Dodecyl-2-O-methoxycarbonyl-glycerol-3-phosphorylcholine.
 m.p. 223° C. (dec.).
 I.R. (nujol): 3350, 1740, 1260 cm⁻¹.
(6) (rac)-1-O-Dodecyl-2-O-ethoxycarbonyl-glycerol-3-phosphorylcholine.
 m.p. 220° C. (dec.).
 I.R. (CHCl₃): 3300, 1740, 1260 cm⁻¹.
(7) (rac)-1-O-Tetradecyl-2-O-methoxycarbonyl-glycerol-3-phosphorylcholine.
 m.p. 203° C. (dec.).
 I.R. (nujol): 3380, 1745, 1265 cm⁻¹.
(8) (rac)-1-O-Hexadecyl-2-O-methoxycarbonyl-glycerol-3-phosphorylcholine.
 m.p. 218° to 232° C. (dec.).
 I.R. (nujol): 3390, 1740, 1100 cm⁻¹.
 N.M.R. (CD₃OD) ppm 0.92 (3H, t, J=5 Hz), 1.2~1.6 (28H, m), 3.28 (9H, s), 3.5~4.6 (10H, m), 3.80 (3H, s), 5.05 (1H, m).
 Anal. Calcd. for C₂₆H₅₄NO₈.H₂O.½CHCl₃ C: 51.55, H: 9.22, N: 2.26. Found: C: 50.89, H: 9.07, N: 2.09.
(9) (rac)-1-O-Octadecyl-2-O-methoxycarbonyl-glycerol-3-(2-pyridinioethyl)phosphate (white solid).
 m.p. 166° C. (dec.).
 I.R. (nujol): 3370, 1755 (shoulder), 1735, 1236 cm⁻¹.
(10) (rac)-1-O-Octadecyl-2-O-methoxycarbonyl-glycerol-3-phosphorylethanolamine (white solid).
 m.p. 196° to 200° C.
 I.R. (nujol): 1740, 1270 cm⁻¹.
(11) (rac)-1-O-Octadecyl-2-O-ethoxycarbonyl-glycerol-3-phosphorylcholine (hygroscopic solid).
 m.p. 220° C. (dec.).
 I.R. (nujol): 3360, 1740, 1260, 1080, 1060 cm⁻¹.
(12) (rac)-1-O-Octadecyl-2-O-propoxycarbonyl-glycerol-3-phosphorylcholine.
 m.p. 210° C. (dec.)
 I.R. (nujol): 3380, 1740, 1250 cm⁻¹.
(13) (rac)-1-O-Octadecyl-2-O-isopropoxycarbonyl-glycerol-3-phosphorylcholine.
 m.p. 240° C. (dec.).
 I.R. (nujol): 3360, 1745, 1260 cm⁻¹.
(14) (rac)-1-O-Octadecyl-2-O-isobutoxycarbonyl-glycerol-3-phosphorylcholine.
 m.p. 213° to 215° C. (dec.).
 I.R. (nujol): 3370, 1745, 1255 cm⁻¹.
(15) (rac)-1-O-Octadecyl-2-O-butoxycarbonyl-glycerol-3-phosphorylcholine.
 m.p. 208° to 213° C. (dec.).
 I.R. (nujol): 3470, 1745, 1255 cm⁻¹.
(16) (rac)-1-O-Octadecyl-2-O-benzyloxycarbonyl-glycerol-3-phosphorylcholine.
 m.p. 172° C. (dec.).
 I.R. (nujol): 3340, 1740, 1250 cm⁻¹.

(17) (rac)-2-O-Methoxycarbonyl-1,2-butanediol-1-phosphorylcholine.
m.p. 98° to 102° C.
I.R. (nujol): 3370, 1735, 1270 cm$^{-1}$.
(18) (rac)-2-O-Methoxycarbonyl-1,2-octadecanediol-1-phosphorylcholine.
m.p. 82° to 85° C.
I.R. (nujol): 3370, 1740, 1460, 1265 cm$^{-1}$.
(19) (rac)-1-s-Octadecyl-2-O-methoxycarbonyl-thioglycerol-3-phosphorylcholine.
m.p. 210° to 214° C. (dec.).
I.R. (nujol): 3350, 1740, 1260 cm$^{-1}$.
(20) (rac)-1-O-Benzyl-2-O-methoxycarbonyl-glycerol-3-phosphorylcholine.
m.p. 69° to 70° C.
I.R. (nujol): 3370, 1745, 1450, 1265, 1085, 965 cm$^{-1}$.
(21) (rac)-2-O-Methoxycarbonyl-3-octadecanoylamino-1,2-propandiol-1-phosphorylcholine.
m.p. 220° C. (dec.).
I.R. (CHCl$_3$): 3300, 2900, 1745, 1260~1190.
(22) (rac)-1-O-Decyl-2-O-methoxycarbonyl-glycerol-3-phosphorylethanolamine.
m.p. 210° C. (dec.).
I.R. (CHCl$_3$): 3250, 2900, 2850, 1740, 1265 cm$^{-1}$.
(23) (rac)-1-O-Decyl-2-O-methoxycarbonyl-glycerol-3-phosphoryl-(N-isopropyl)ethanolamine.
m.p. 123° to 125° C.
I.R. (nujol): 2700, 2530, 1745, 1260, 1230 cm$^{-1}$.

EXAMPLE 8

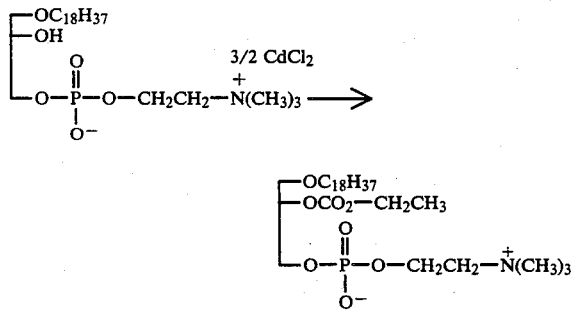

To a rapidly stirred mixture of (rac)-1-O-octadecyl-glycerol-3-phosphorylcholine 3/2CdCl$_2$ (10.71 g) and glass beads (133 ml) was added, dropwise over 2.5 hours, a solution of ethyl chloroformate (17.21 g) in dry chloroform (40 ml) and subsequently a solution of dry pyridine (12.54 g) in dry chloroform (80 ml) dropwise over 2 hours at 0° C. After one hour, the solution was allowed to stand for 15.5 hours at ambient temperature, and then glass beads were removed by filtration. The filtrate was evaporated and acetone was added to the residue. The crude crystals were obtained by filtration, dissolved in 130 ml of chloroform-methanol-water (5:4:1), and the solution was passed through a mixed-bed ion-exchange column containing a mixture of Amberlite IR-45 (OH$^-$) (64 g) and IRC-50 (H$^+$) (32 g). The column was washed with 260 ml of the same solvent, and the combined eluates were evaporated under reduced pressure. Purification of the residue was carried out by chromatography on silica gel (200 g, elution by chloroform:methanol:water, 65:25:4, by vol). The combined eluates containing the desired product was evaporated to dryness. The crude solid was recrystallized from chloroform-acetone to yield 0.93 g of (rac)-1-O-octadecyl-2-O-ethoxycarbonyl-glycerol-3-phosphorylcholine as a hygroscopic solid.
m.p. 220° C. (dec.)
I.R. (nujol): 3360, 1740, 1260, 1080, 1060 cm$^{-1}$.
N.M.R. (CD$_3$OD) ppm 0.60~1.80 (38H, m), 3.00~3.72 (6H, m), 3.24 (9H, s), 3.84~4.40 (6H, m), 4.80~5.04 (1H, m).
Anal. Calcd. for C$_{29}$H$_{60}$NO$_8$P.H$_2$O C: 58.07, H: 10.42, N: 2.34. Found: C: 57.65, H: 9.91, N: 2.24.

EXAMPLE 9

The following compounds were prepared according to a similar manner to that of Example 8.
(1) (rac)-1-O-Hexyl-2-O-methoxycarbonyl-glycerol-3-phosphorylcholine (oil).
I.R. (CHCl$_3$): 3300, 2900, 2850, 1740, 1270 cm$^{-1}$.
(2) (rac)-1-O-Octyl-2-O-methoxycarbonyl-glycerol-3-phosphorylcholine.
m.p. 213° to 216° C.
I.R. (nujol): 3400, 1750, 1250 cm$^{-1}$.
(3) (rac)-1-O-Decyl-2-O-methoxycarbonyl-glycerol-3-phosphorylcholine.
m.p. 230° C. (dec.).
I.R. (nujol): 3360, 1730, 1260 cm$^{-1}$.
(4) (rac)-1-O-Decyl-2-O-methoxycarbonyl-glycerol-3-phosphoryl-(N-methyl)ethanolamine.
m.p. 175° C.
I.R. (CHCl$_3$): 3350, 2900, 2850, 1740, 1270 cm$^{-1}$.
(5) (rac)-1-O-Dodecyl-2-O-methoxycarbonyl-glycerol-3-phosphorylcholine.
m.p. 223° C. (dec.).
I.R. (nujol): 3350, 1740, 1260 cm$^{-1}$.
(6) (rac)-1-O-Dodecyl-2-O-ethoxycarbonyl-glycerol-3-phosphorylcholine.
m.p. 220° C. (dec.).
I.R. (CHCl$_3$): 3300, 1740, 1260 cm$^{-1}$.
(7) (rac)-1-O-Tetradecyl-2-O-methoxycarbonyl-glycerol-3-phosphorylcholine.
m.p. 203° C. (dec.).
I.R. (nujol): 3380, 1745, 1265 cm$^{-1}$.
(8) (rac)-1-O-Hexadecyl-2-O-methoxycarbonyl-glycerol-3-phosphorylcholine.
m.p. 218° to 232° C. (dec.).
I.R. (nujol): 3390, 1740, 1100 cm$^{-1}$.
(9) (rac)-1-O-Octadecyl-2-O-methoxycarbonyl-glycerol-3-phosphorylcholine (hygroscopic solid).
m.p. 275° C. (dec.).
I.R. (CHCl$_3$): 3400, 1745, 1630, 1090 cm$^{-1}$.
(10) (rac)-1-O-Octadecyl-2-O-methoxycarbonyl-glycerol-3-(2-pyridinioethyl)phosphate (white solid).
m.p. 166° C. (dec.)
I.R. (nujol): 3370, 1755 (shoulder), 1735, 1235 cm$^{-1}$.
(11) bromide salt of (rac)-1-O-Octadecyl-2-O-methoxycarbonyl-glycerol-3-(ethyl 2-trimethylammonioethyl)phosphate.
m.p. 135° C.
I.R. (nujol): 3400, 1750, 1260 cm$^{-1}$.
(12) (rac)-1-O-Octadecyl-2-O-methoxycarbonyl-glycerol-3-phosphorylethanolamine (white solid).
m.p. 196° to 200° C.
I.R. (nujol): 1740, 1270 cm$^{-1}$.
(13) (rac)-1-O-Octadecyl-2-O-methoxycarbonyl-glycerol-3-(3-trimethylammoniopropyl)phosphonate (white solid).
m.p. 220° C. (dec.).
I.R. (nujol): 3300, 1740, 1265, 1200, 1050 cm$^{-1}$.
(14) (rac)-1-O-Octadecyl-2-O-propoxycarbonyl-glycerol-3-phosphorylcholine.

m.p. 210° C. (dec.).
I.R. (nujol): 3380, 1740, 1250 cm$^{-1}$.
(15) (rac)-1-O-Octdecyl-2-O-isopropoxycarbonyl-glycerol-3-phosphorylcholine.
m.p. 240° C. (dec.).
I.R. (Nujol): 3360, 1745, 1260 cm$^{-1}$.
(16) (rac)-1-O-Octadecyl-2-O-isobutoxycarbonyl-glycerol-3-phosphorylcholine.
m.p. 213° to 215° C. (dec.)
I.R. (nujol): 3370, 1745, 1255 cm$^{-1}$.
(17) (rac)-1-O-Octadecyl-2-O-butoxycarbonyl-glycerol-3-phosphorylcholine.
m.p. 208° to 213° C. (dec.).
I.r. (nujol): 3470, 1745, 1255 cm$^{-1}$.
(18) (rac)-1-O-Octadecyl-2-O-benzyloxycarbonyl-glycerol-3-phosphorylcholine.
m.p. 172° C. (dec.).
I.R. (nujol):3340, 1740, 1250 cm$^{-1}$.
(19) (rac)-2-O-Methoxycarbonyl-1,2-butanediol-1-phosphorylcholine.
m.p. 98° to 102° C.
I.R. (nujol): 3370, 1735, 1270 cm$^{-1}$.
(20) (rac)-2-O-methoxycarbonyl-1,2-octadecanediol-1-phosphorylcholine.
m.p. 82° to 85° C.
I.R. (nujol): 3370, 1740, 1460, 1265 cm$^{-1}$.
(21) (rac)-1-s-Octadecyl-2-O-methoxycarbonyl-thio-glycerol-3-phosphorylcholine.
m.p. 210° to 214° C. (dec.).
I.R. (nujol): 3350, 1740, 1260 cm$^{-1}$.
(22) (rac)-1-O-Benzyl-2-O-methoxycarbonyl-glycerol-3-phosphorylcholine.
m.p. 69° to 70° C.
I.R. (nujol): 3370, 1745, 1450, 1265, 1085, 965 cm$^{-1}$.
(23) (rac)-2-O-Methoxycarbonyl-3-octadecanoylamino-1,2-propandiol-1-phosphorylcholine.
m.p. 220° C. (dec.).
I.R. (CHCl$_3$): 3300, 2900, 1745, 1260~1190 cm$^{-1}$.
(24) (rac)-1-O-Decyl-2-O-methoxycarbonyl-glycerol-3-phosphorylethanolamine.
m.p. 210° C. (dec.).
I.R. (CHCl$_3$): 3250, 2900, 2850, 1740, 1265 cm$^{-1}$.
N.M.R. (CD$_3$OD)ppm 0.99 (3H, t, J=5.5 Hz), 1.12~1.68 (16H, m), 3.15~4.30 (10H, m), 3.76 (3H, s), 4.95 (1H, m).
(25) (rac)-1-O-Decyl-2-O-methoxycarbonyl-glycerol-3-phosphoryl-(N-isopropyl)ethanolamine.
m.p. 123° to 125° C.
I.R. (nujol): 2700, 2530, 1745, 1260, 1230 cm$^{-1}$.
N.M.R. (CD$_3$OD)ppm 0.90 (3H, t, J=6 Hz), 1.19~1.68 (22H, m), 3.20~4.08 (11H, m), 3.79 (3H, s), 4.99 (1H, m).

EXAMPLE 10

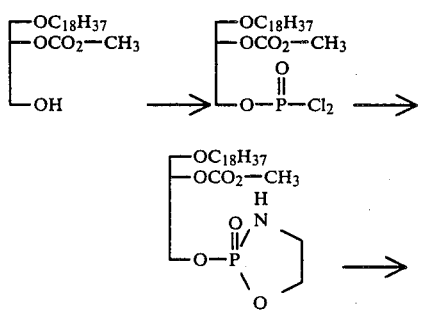

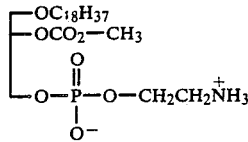

To a stirred mixture of phosphorus oxychloride (1.35 g) and triethylamine (0.99 g) in dry chloroform (17 ml) was added, dropwise over 20 minutes, a solution of (rac)-1-O-octadecyl-2-O-methoxycarbonyl-glycerol (3.01 g) in dry chloroform (9 ml) at 0° to 5° C. to give a solution containing (rac)-1-O-octadecyl-2-O-methoxycarbonyl-glycerol-3-phosphoric acid chloride. After one hour, a mixture of monoethanolamine (0.55 g), and triethylamine (1.82 g) was added dropwise over 20 minutes to the solution at 0° to 5° C. followed by stirring for 30 minutes. The resulting mixture containing 2-{(rac)-1-O-octadecyl-2-O-methoxycarbonyl-glycerol}-2-oxo-1,3,2-oxazaphospholidine was then washed with aqueous hydrochloric acid and brine, dried, and evaporated to dryness. The residue was dissolved in a mixture of 50% aqueous formic acid (40 ml) and methanol (10 ml) followed by stirring for 30 minutes. The solvents were then removed under reduced pressure. The oily residue was crystallized from ethanol to yield 3.42 g of (rac)-1-O-octadecyl-2-O-methoxycarbonyl-glycerol-3-phosphorylethanolamine as a white solid, which was purified by recrystallization from ethanol.
m.p. 196° to 200° C.
I.R. (Nujol): 1740, 1270 cm$^{-1}$.
N.M.R. (CF$_3$CO$_2$H)ppm 0.91~2.08 (37H, m), 3.40~4.92 (11H, m), 3.96 (3H, s), 5.32 (1H, brS).
Anal. Calcd. for C$_{25}$H$_{52}$NO$_8$P.2H$_2$O C: 52.81, H: 9.69, N: 2.01. Found: C: 53.46, H: 10.05, N: 2.49.

EXAMPLE 11

The following compounds were prepared according to a similar manner to that of Example 10.
(1) (rac)-1-O-Decyl-2-O-methoxycarbonyl-glycerol-3-phosphoryl-(N-methyl)ethanolamine.
m.p. 175° C.
I.R. (CHCl$_3$): 3350, 2900, 2850, 1740, 1270 cm$^{-1}$.
N.M.R. (CD$_3$OD)ppm 0.99 (3H, t, J=5.5 Hz), 1.06~1.67 (16H, m), 2.72 (3H, s), 3.16~4.16 (10H, m), 3.73 (3H, s), 4.92 (1H, m).
Anal. Calcd. for C$_{18}$H$_{38}$NO$_8$P C: 50.58, H: 8.96, N: 3.28. Found: C: 50.15, H: 9.01, N: 3.33.
(2) (rac)-1-O-Decyl-2-O-methoxycarbonyl-glycerol-3-phosphorylethanolamine.
m.p. 210° C. (dec.).
I.R. (CHCl$_3$): 3250, 2900, 2850, 1740, 1265 cm$^{-1}$.
N.M.R. (CD$_3$OD)ppm 0.99 (3H, t, J=5.5 Hz), 1.12~1.68 (16H, m), 3.15~4.30 (10H, m), 3.76 (3H, s), 4.95 (1H, m).
(3) (rac)-1-O-Decyl-2-O-methoxycarbonyl-glycerol-3-phosphoryl-(N-isopropyl)ethanolamine.
m.p. 123° to 125° C.
I.R. (nujol): 2700, 2530, 1745, 1260, 1230 cm$^{-1}$.
N.M.R. (CD$_3$OD)ppm 0.90 (3H, t, J=6 Hz), 1.19~1.68 (22H, m), 3.20~4.08 (11H, m), 3.79 (3H, s), 4.99 (1H, m).
What is claimed is:
1. A compound of the formula:

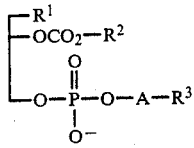

wherein $R^1$ is $C_{1-20}$ alkyl, $C_{1-20}$ alkoxy, $C_{16-20}$ alkylthio or phenyl(lower)alkoxy;

$R^2$ is lower alkyl or phenyl(lower)alkyl;

A is lower alkylene; and $R^3$ is a group of the formula:

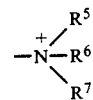

in which $R^5$, $R^6$ and $R^7$ are each hydrogen or lower alkyl;

and pharmaceutically acceptable salt thereof.

2. The compound of claim 1, wherein $R^1$ is $C_{1-20}$ alkoxy.

3. The compound of claim 2, wherein $R^2$ is lower alkyl.

4. The compound of claim 3, which is (rac)-1-O-octadecyl-2-O-methoxycarbonyl-glycerol-3-phosphorylcholine.

5. The compound of claim 1, wherein A is ethylene.

6. A pharmaceutical composition, for treating hypertension, comprising an effective amount of a compound of claim 1, as an effective ingredient, in association with a pharmaceutically acceptable, substantially nontoxic carrier or excipient.

7. A method for treating hypertension which comprises administering an effective amount of the compound of claim 1 to a human being.

* * * * *